United States Patent [19]

Ott et al.

[11] Patent Number: 4,952,733
[45] Date of Patent: Aug. 28, 1990

[54] PREPARATION OF 1,3,5-TRIAMINO-2,4,6-TRINITROBENZENE FROM 3,5-DICHLORANISOLE

[75] Inventors: Donald G. Ott, Los Alamos; Theodore M. Benziger, Santa Fe, both of N. Mex.

[73] Assignee: The United States of America as represented by the United States Department of Energy, Washington, D.C.

[21] Appl. No.: 289,653

[22] Filed: Dec. 21, 1988

[51] Int. Cl.$^5$ .................. C07C 209/10; C07C 43/205; C07C 205/06
[52] U.S. Cl. .................................... 564/406; 568/588; 568/933
[58] Field of Search ................ 564/399, 406; 568/588, 568/933

[56] References Cited

U.S. PATENT DOCUMENTS

| | | | |
|---|---|---|---|
| 3,166,594 | 1/1965 | Harris et al. | 260/580 |
| 3,404,184 | 10/1968 | Oesterling | 260/581 |
| 4,032,377 | 1/1977 | Benziger | 149/105 |
| 4,090,862 | 5/1978 | Thomas et al. | 71/98 |

FOREIGN PATENT DOCUMENTS 0057871  8/1982  European Pat. Off. .

OTHER PUBLICATIONS

"Prep. of 1,3,5–Triamino–2,4,6–Trinitrobenzene, etc.", J. Energy Mater., Ott et al. (1987), 5 (3–4), 343–54 in Chem. Abst., 109, 1988; 109: 128,473t.

Primary Examiner—Richard L. Raymond
Assistant Examiner—P. O'Sullivan
Attorney, Agent, or Firm—Samuel M. Freund; Paul D. Gaetjens; William R. Moser

[57] ABSTRACT

Preparation of 1,3,5-triamino-2,4,6-trinitrobenzene (TATB) from 3,5-dichloroanisole. Nitration of 3,5-dichloroanisole under relatively mild conditions gave 3,5-dichloro-2,4,6-trinitroanisole in high yield and purity. Ammonolysis of this latter compound gave the desired TATB. Another route to TATB was through the treatment of the 3,5-dichloro-2,4,6-trinitroanisole with thionyl chloride and dimethylformamide to yield 1,3,5-trichloro-2,4,6-trinitrobenzene. Ammonolysis of this product produced TATB.

4 Claims, 4 Drawing Sheets

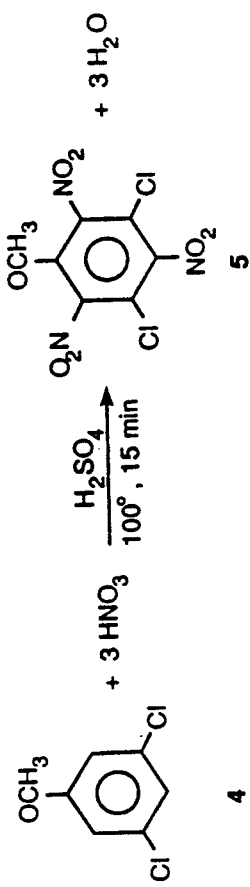
*Fig. 2a*
*Fig. 2b*
*Fig. 2c*

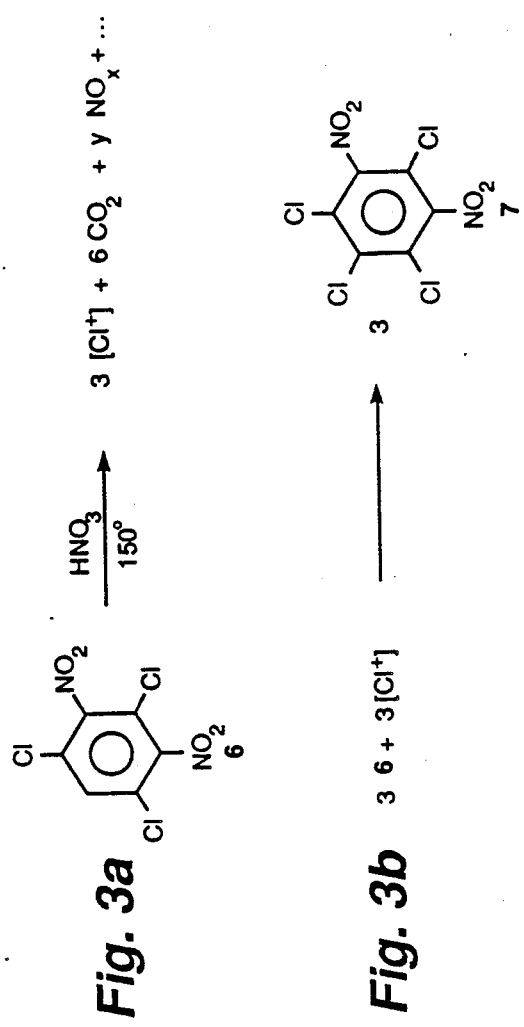

PREPARATION OF 1,3,5-TRIAMINO-2,4,6-TRINITROBENZENE FROM 3,5-DICHLORANISOLE

The United States Government has rights in this invention pursuant to Contract No. W-7405-ENG-36 between the U.S. Department of Energy and the University of California.

BACKGROUND OF THE INVENTION

The present invention relates generally to the preparation of triaminotrinitrobenzene (TATB), and more specifically to the preparation of TATB from 3,5-dichloroanisole (DCA).

Triaminotrinitrobenzene is an explosive having unusual insensitivity, stability at high temperature, and respectable performance. It is insoluble in organic solvents and has a melting point above 400° C. TATB was prepared in 1887 from tribromotrinitrobenzene. It has also been prepared on a laboratory scale from 2,4,6-trinitrotoluene through selective reduction of the 4-nitro group, nitration to pentanitroaniline, and then ammonolysis. Currently, the manufacture of TATB (1) on a large scale begins with 1,3,5-trichlorobenzene (TCB, 2) which is nitrated to give 1,3,5-trichloro-2,4,6-trinitrobenzene (TCTNB, 3) as shown in FIGS. 1a and 1b hereof. The nitration step requires severe conditions of high temperature, long reaction time, and oleum, and results in significant quantities of by-products.

Accordingly, it is an object of the present invention to provide a more efficient process for synthesizing TATB.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects and in accordance with the purpose of the present invention, as embodied and broadly described herein, the method of preparing TATB of this invention includes the steps of nitrating 3,5-dichloroanisole to produce 3,5-dichloro-2,4,6-trinitroanisole, and ammonolyzing the 3,5-dichloro-2,4,6-trinitroanisole to yield TATB.

In a further aspect of the present invention, in accordance with its objects and purposes, the method of preparing TATB of this invention includes the steps of nitrating 3,5-dichloroanisole to produce 3,5-dichloro-2,4,6-trinitroanisole, chlorinating the 3,5-dichloro-2,4,6-trinitroanisole so produced to yield 1,3,5-trichloro-2,4,6-trinitrobenzene, and ammonolyzing the 1,3,5-trichloro-2,4,6-trinitrobenzene to yield TATB.

Benefits and advantages of the present invention include ease of nitration of the starting materials, the purity of the nitrated intermediates, and the rapidity and high yield of the reaction. As a result, development of a continuous process appears to be possible.

BRIEF DESCRIPTION OF THE DRAWINGS

The accompanying drawings, which are incorporated in and form a part of the specification, illustrate two embodiments of the present invention and, together with the description, serve to explain the principles of the invention. In the drawings:

FIG. 1 illustrates the present commercial, large-scale synthesis of TATB. FIG. 1a shows the nitration of the starting material, 1,3,5-trichlorobenzene (2) to the intermediate 1,3,5-trichloro-4,6-trinitrobenzene (3), while

FIG. 2 illustrates the synthesis of TATB according to the teachings of the present invention. FIG. 2a shows the nitration of the starting material, 3,5-dichloranisole (4) to 3,5-dichloro-2,4,6-trinitroanisole (5), while FIG. 2b shows the ammonolysis of this latter compound to TATB (1). FIG. 2c shows an alternative path to reach the desired TATB. The 3,5-dichloro-2,4,6-trinitroanisole (5) is first further chlorinated to yield 1,3,5-trichloro-2,4,6-trinitrobenzene, then ammonolyzed to yield TATB (1) according to the reaction described in FIG. 1b hereof.

FIG. 3 illustrates the nitrated chlorobenzenes produced as a by-product from the commercial, large-scale synthesis currently employed and illustrated in FIG. 1 hereof.

DETAILED DESCRIPTION OF THE INVENTION

Briefly, the present invention teaches the preparation of 1,3,5-triamino-2,4,6-trinitrobenzene, TATB, from the nitration of 3,5-dichloranisole under relatively mild conditions in high yield and purity. The intermediate, 3,5-dichloro-2,4,6-trinitroanisole, is readily ammonolyzed to the TATB desired product. Another route is to first chlorinate this intermediate to give 1,3,5-trichloro-2,4,6-trinitrobenzene, which then may be ammonolyzed to produce TATB.

Figure 1A:
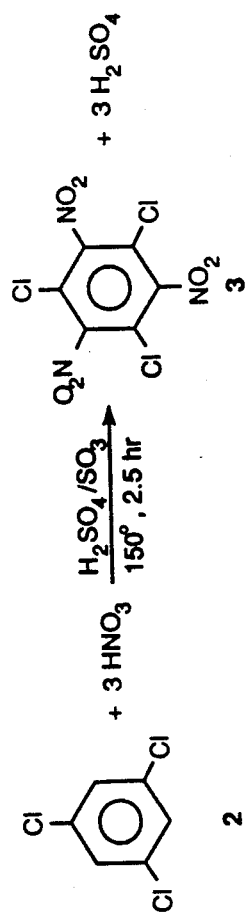
Figure 1B:
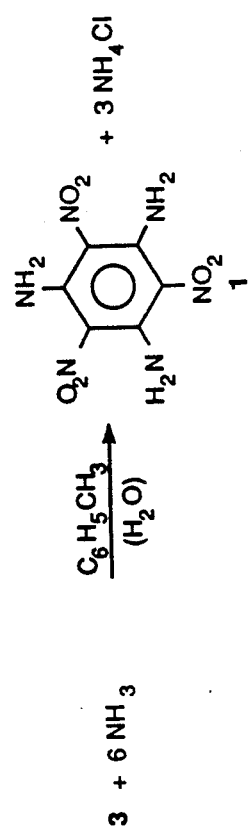
FIG. 1b shows the ammonolysis of this latter compound to TATB (1).

Reference will now be made in detail to the present preferred embodiments of the invention, examples of which are illustrated in the accompanying drawings. Turning to FIG. 1, the large-scale, commercial preparation of TATB is illustrated. The conditions necessary to effect the introduction of the third nitro group into the trichloro compound starting material 2 to produce 3 are quite severe. An excess of 90–95% nitric acid (4.35 moles per mole of 2) and 25–30% oleum (20 moles) are used at a reaction temperature of 150° C. with vigorous stirring for 2.5 hours, as is described in "Method for the Production of High-Purity Triaminotrinitrobenzene," U.S. Pat. No. 4,032,377, issued to T. M. Benziger in Jun. 1977, the teachings of which are hereby incorporated by reference herein. After quenching the mixture with water, the product was isolated in 91% yield and 89% purity. The by-products were other nitrated chlorobenzenes, primarily 1,3,5-trichloro-2,4-dinitrobenzene (6) (3%), and 1,2,3,5-tetrachloro-4,6-dinitrobenzene (7) (8%) as illustrated in FIG. 3 hereof. The conversion was 0.80 mole of 3 per mole of 2. For subsequent ammonolysis of 3 to 1, it was unnecessary to remove either 6 or 7, since both compounds are virtually unreactive toward ammonia. The tetrachloro compound 7 was formed from the dinitro intermediate 6 and chlorine (or a chlorinating species) that had been generated by oxidation of 6. For the optimum conditions of time, temperature, and concentrations investigated, it was shown that a portion of the intermediate 6 (equivalent to approximately 0.03 mole per mole of the starting material 2) was oxidized to give carbon dioxide (0.18 mole) and the active chlorine (0.09 mole), which then reacted with additional 6 (equivalent to 0.09 mole of 2) to give compound 7 (0.09 mole).

Nitration of starting material 4 would be expected to proceed more rapidly than nitration of compound 2 because of the activating effect of the methoxyl group on electrophilic aromatic substitution. The reaction illustrated in FIG. 2a hereof was indeed found to proceed with excellent yield at lower temperature (100° C.) without the necessity of an excess of nitric acid or the use of oleum. No by-product analogous to 7 was detected. Complete conversions of the starting material were obtained when the excess of nitric acid was merely five percent over the stoichiometric amount. For this latter result, a temperature of 125° C. was employed, and the reaction allowed to proceed for two hours. However, the use of a minimum of nitric acid has a distinct advantage for synthesis of the nitrogen-15 labeled analog.

Figure 4:
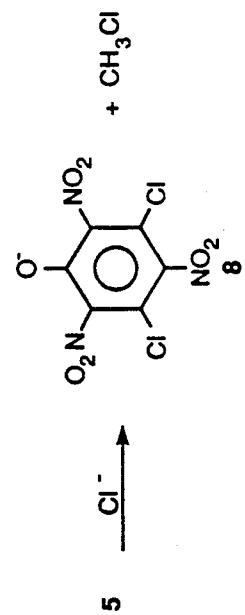
FIG. 4 illustrates a biproduct from the synthesis according to the teachings of the present invention illustrated in FIG. 2 hereof.

Displacements of both the chloro and the methoxyl groups of 5 by ammonia occured readily to give 1. Ammonolysis of reactions using limited amounts of ammonia give a mixture of 1 and starting materials 3 or 5, with only very small quantities of mono- and diamino compounds. However, from reactions in which mixtures of 3 and 5 were treated with limited quantities of ammonia, it was found that 5 reacted several times faster than 3. For certain applications, it is desirable that TATB be produced with a median particle size of about 50 μm. Ammonolysis at low temperatures results in 1 precipitating as extremely small crystals. However, extensive side reactions were found to occur when ammonolysis of 5 was carried out at temperatures above 50° C. FIG. 4 shows the principal side reaction in the ammonolysis of 5. This reaction does not occur at low temperatures since ammonium chloride is insoluble in toluene, and when better solvents for the chloride, such as dimethylformamide or dimethyl sulfoxide, are employed, or added to the toluene, the yield of 1 is substantially reduced, even at low temperature. The material was thus of small size (90% of the particles were smaller than 10 μm). However, the purity of 1, which was obtained in yields greater than 95% was unaffected by side reactions when the ammonolysis reactions were conducted at ambient temperature and in relatively non-polar solvents.

Recrystallization of TATB is impractical on a large scale. When small quantities having extremely high purity are desired, however, TATB may be recrystallized from dimethyl sulfoxide or from diphenyl ether.

Direct conversion from 5 to 3 can be achieved in excellent yield and purity when a stoichiometric amount of dimethy formamide is employed. With catalytic amounts, the reaction is slow, and there is some reduction of nitro groups to azoxy. Although producing 3 from 5 requires an additional step over its production from 2, the overall yield and conversion are higher, the product is of high purity (no by-product analogous to 7), conditions for the nitration of 4 are milder and offer the possibility for a continuous process, with less waste being generated.

Having generally described the invention, the specific embodiments hereof are demonstrated in the following examples.

EXAMPLE I

Preparation of 3,5-dichloro-2,4,6-trinitroanisole (5) 3,5-dichloroanisole (35.4 g, 0.20 mole) was added over a period of 2 min. to a stirred mixture of nitric acid (90%, 50 ml, 1.0 mol) and sulfuric acid (94%, 115 ml) in a flask cooled in an ice bath. The temperature of the mixture was found to rise to 50° C. After 3 min. the ice bath was removed, and the mixture was heated from 35° C. to 100° C. over a period of 8 min. where it was held for 15 min. The mixture was then cooled to room temperature and poured onto ice. The product was filtered, washed with water, and dried (61.5 g, 98.6% yield). The melting point of the resulting compound was 94°–95° C. (95°–95.5° C. after recrystallization from toluene-hexane).

EXAMPLE II

Preparation of 1,3,5-trichloro-2,4,6-trinitrobenzene (3)

Thionyl chloride (0.20 ml, 0.027 mol) and dimethylformamide (0.15 ml, 0.022 mol) was added to a solution of 5 (0.624 g, 0.020 mol) in toluene (2 ml) at 50° C. The mixture was stirred and heated to 95° C. over a period of 15 min. and maintained at that temperature for another hour. The pale yellow solution was washed with water, dried over magnesium sulfate, treated with activated carbon, filtered, and evaporated to give a cream-colored solid (0.600 g, 95% yield). The melting point of the material so obtained was 194°–195° C. (195°–196° C. after recrystallization from acetic acid).

EXAMPLE III

A. Preparation of 1,3,5-triamino-2,4,6-trinitrobenzene (1) according to FIG. 2b hereof A solution of 5 (3.12 g, 0.010 mol) in toluene (40 ml) was placed in a stainless-steel autoclave having a Teflon-covered stirring bar and the system evacuated to the vapor pressure of toluene (30–40 mm of Hg). Ammonia (5.5 mmol) was admitted to the autoclave over a period of 30 min. during which time the temperature rose to about 30° C. The autoclave was opened, the mixture filtered, and the bright yellow product was washed sequentially with toluene, hot water, and acetone, and dried (2.47 g, 96% yield).

B. Preparation of 1,3,5-triamino-2,4,6-trinitrobenzene (1) according to FIG. 2b hereof Ammonia was introduced over the surface of a vigorously stirred solution of 5 (2.56 g, 8.2 mmol) in toluene (40 ml). After about 7 hours the supernatant solution over the pale yellow precipitate became colorless, and analysis showed the absence of starting material and intermediates. The ammonia flow was halted, and the product was isolated as in A above (1.99 g, 94% yield). Recrystallization of TATB from either dimethyl sulfoxide (5 g/l at 145° C.) or from diphenyl ether (2 g/l at 220° C.) removed trace impurities with essentially complete recovery of the TATB.

The foregoing description of two preferred embodiments of the invention has been presented for purposes of illustration and description. It is not intended to be exhaustive or to limit the invention to the precise form disclosed, and obviously many modifications and variations are possible in light of the above teaching. For example, in view of the rapidity of the reactions involved in the synthesis of TATB according to the teachings of the present invention, and the relatively mild conditions employed, development of a continuous process would be apparent to one having ordinary skill in the synthesis of explosives after studying the details of the subject disclosure. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What we claim is:

1. A method of preparing 1,3,5-triamino-2,4,6-trinitrobenzene from 3,5-dichloroanisole, comprising the steps of:

a. nitrating 3,5-dichloroanisole to produce 3,5-dichloro-2,4,6-trinitroanisole;
   b. chlorinating the 3,5-dichloro-2,4,6-trinitroanisole so produced to yield 1,3,5-trichloro-2,4,6-trinitrobenzene; and
   c. ammonolyzing the 1,3,5-trichloro-2,4,6-trinitrobenzene.

2. The method as described in claim 1, wherein said step of nitrating 3,5-dichloroanisole includes the use of nitric acid and sulfuric acid.

3. The method as described in claim 1, wherein said step of chlorinating the 3,5-dichloro-2,4,6-trinitroanisole includes the use of thionyl chloride in toluene.

4. The method as described in claim 1, wherein said step of ammonolyzing said 1,3,5-trichloro-2,4,6-trinitrobenzene includes the use of ammonia in toluene.

* * * * *